(12) United States Patent
McBride et al.

(10) Patent No.: US 8,202,990 B2
(45) Date of Patent: Jun. 19, 2012

(54) POLO-LIKE KINASE INHIBITORS

(75) Inventors: Christopher McBride, San Diego, CA (US); Zhe Nie, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 137 days.

(21) Appl. No.: 12/680,142

(22) PCT Filed: Sep. 25, 2008

(86) PCT No.: PCT/US2008/077746
§ 371 (c)(1),
(2), (4) Date: May 11, 2010

(87) PCT Pub. No.: WO2009/042806
PCT Pub. Date: Apr. 2, 2009

(65) Prior Publication Data
US 2010/0222575 A1    Sep. 2, 2010

Related U.S. Application Data

(60) Provisional application No. 60/975,127, filed on Sep. 25, 2007.

(51) Int. Cl.
*C07D 487/04*    (2006.01)

(52) U.S. Cl. .................................................. 540/501
(58) Field of Classification Search .................. 540/501
See application file for complete search history.

(56) References Cited

U.S. PATENT DOCUMENTS

| 7,517,873 | B2 * | 4/2009 | Chen ............................ 514/221 |
| 8,003,785 | B2 * | 8/2011 | Cai et al. ........................ 540/501 |
| 8,026,234 | B2 * | 9/2011 | Ichikawa et al. ............... 514/221 |
| 2009/0281092 | A1 | 11/2009 | Cao et al. |

FOREIGN PATENT DOCUMENTS

WO    WO/2008/113711    9/2008

OTHER PUBLICATIONS

Gordon, et al., "The Chemists Companion," 1972, P27, John Wiley & Sons, New York.

* cited by examiner

*Primary Examiner* — Bruck Kifle
(74) *Attorney, Agent, or Firm* — David M. Stemerick

(57) ABSTRACT

The present invention relates generally to processes of making 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide and Form A of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide.

1 Claim, No Drawings

US 8,202,990 B2

POLO-LIKE KINASE INHIBITORS

FIELD OF THE INVENTION

The present invention relates generally to chemical synthesis and a certain polymorphic form.

BACKGROUND OF THE INVENTION

Kinases are responsible for the control of a wide variety of signal transduction processes by phosphorylation of their target proteins. Kinases regulated processes include proliferation, growth, differentiation, metabolism, cell cycle events, apoptosis, motility, transcription, and translation. Kinases can function, either directly or indirectly, to activate, inactivate, or modulate the activity of the target protein. These target proteins may include, for example, metabolic enzymes, regulatory proteins, receptors, cytoskeletal proteins, ion channels or pumps, or transcription factors.

Polo-like kinases (PLKs including PLK1, PLK2, PLK3 and PLK4) are serine/threonine protein kinases that are involved in the regulation of the cell cycle. In mammalian cells, PLK1 levels increase during mitosis. Target proteins for PLKs include cyclin B, a cohesin subunit of the mitotic spindle, subunits of the anaphase promoting complex, and mammalian kinesin-like protein 1 and other motor proteins. PLK1 has a role in the regulation of CDKs through phosphorylation and activation of Cdc25C leading to activation of CDK1 which is involved in cell division processes. 4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide is an inhibitor of PLKs, particularly PLK1.

SUMMARY OF THE INVENTION

The present invention provides a process for making 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide, comprising the steps of:

a) reacting a compound of formula (1)

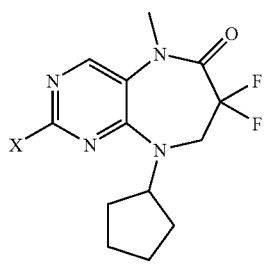

(1)

wherein X is a suitable leaving group with 4-amino-3-methoxy benzoic acid to give 4-(9-cyclopentyl-7,7-difluoro-5-methyl-6-oxo-6,7,8,9-tetrahydro-5H-pyrimido[5,4-b][1,4]diazepin-2-ylamino)-3-methoxybenzoic acid;

b) optional conversion of 4-(9-cyclopentyl-7,7-difluoro-5-methyl-6-oxo-6,7,8,9-tetrahydro-5H-pyrimido[5,4-b][1,4]diazepin-2-ylamino)-3-methoxybenzoic acid to a compound of formula (2)

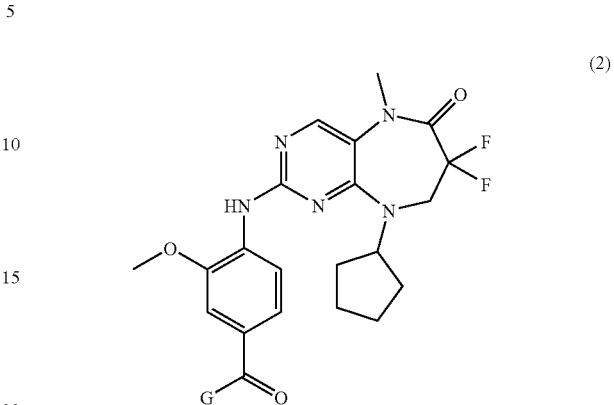

(2)

wherein G is a suitable activating group; and c) coupling 4-(9-cyclopentyl-7,7-difluoro-5-methyl-6-oxo-6,7,8,9-tetrahydro-5H-pyrimido[5,4-b][1,4]diazepin-2-ylamino)-3-methoxybenzoic acid or a compound of formula (2) with 1-methylpiperidin-4-amine.

The present invention also provides a process for making Form A polymorph of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide, comprising crystallizing 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide from a solvent.

As used herein "Form A" refers to 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A.

The present invention also provides pharmaceutical compositions, comprising: 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A and a pharmaceutically acceptable excipient.

The invention provides a method of treating conditions associated with PLK, comprising: administering to a patient in need thereof an effective amount of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A. Further, the present invention provides the use of Form A for the manufacture of a medicament for the treatment of conditions associated with PLK.

The present invention also provides an article of manufacture: comprising 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A and a label. Also provided are kits comprising at least one 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A, a label, and apparatus for administration of the inhibitor.

General synthetic procedures for the present process are set forth in Scheme A. All substituents, unless otherwise indicated, are as previously defined. The products in Scheme A can be recovered by conventional methods including extraction, evaporation, precipitation, chromatography, crystallization, trituration, and the like.

Scheme A

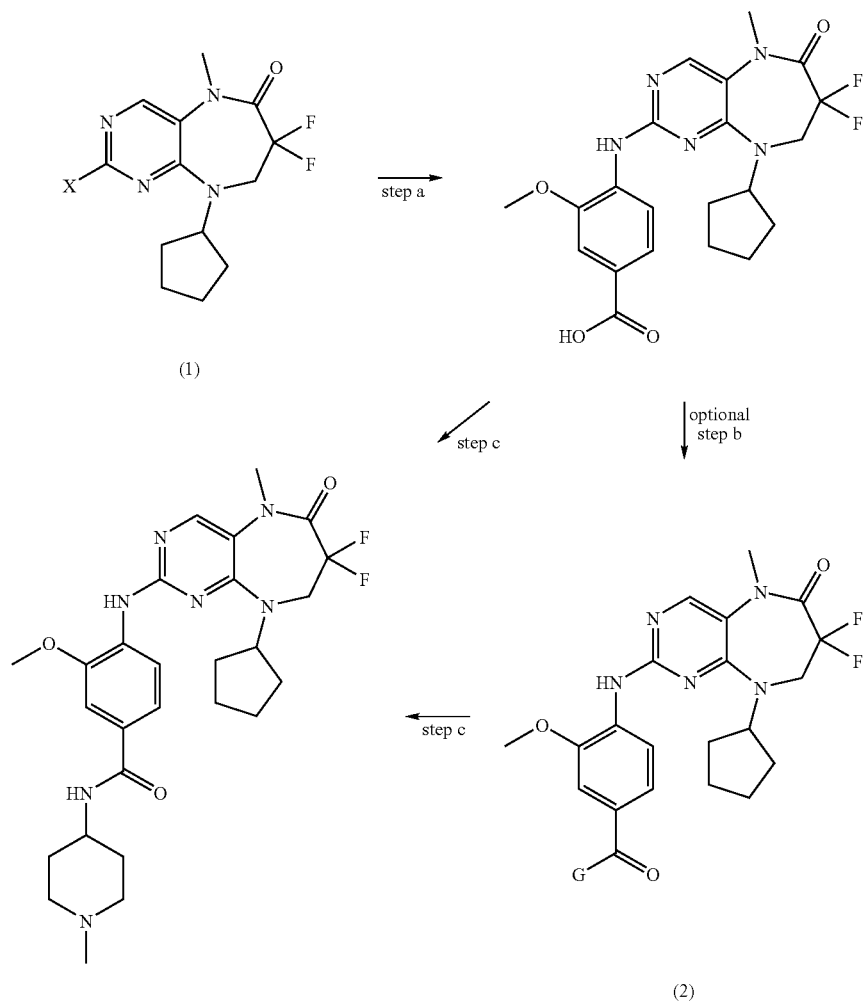

Scheme A, step a, depicts the reaction of a compound of formula (1) with 4-amino-3-methoxy benzoic acid to give 4-(9-cyclopentyl-7,7-difluoro-5-methyl-6-oxo-6,7,8,9-tetrahydro-5H-pyrimido[5,4-b][1,4]diazepin-2-ylamino)-3-methoxybenzoic acid. A compound of formula (1) is one wherein X is a suitable leaving group. A suitable leaving groups is capable of being displaced under alkylating conditions, for example halogens, such as chloro, bromo, iodo; sulfonyloxy groups, such as trifluoromethanesulfonyloxy, mesyloxy, benzenesulfonyloxy, tosyloxy, and nosyloxy; and the like. For example, the reaction is carried out in a suitable solvent, such as lower alcohols, including ethanol, isopropanol, and t-butanol. The reaction is generally carried out in the presence of an acid, such as aqueous hydrochloric acid or aqueous sulfuric acid. Such reactions generally are carried out at temperature of from about 60° C. to the reflux temperature of the chosen solvent and typically require 12 to 72 hours.

Scheme A, step b, depicts the optional reaction of 4-(9-cyclopentyl-7,7-difluoro-5-methyl-6-oxo-6,7,8,9-tetrahydro-5H-pyrimido[5,4-b][1,4]diazepin-2-ylamino)-3-methoxybenzoic acid to give a compound of formula (2). A compound of formula (2) is one in which G is a suitable activating group. Such groups are well known in the art and include halogens, such a chloro and bromo, activating groups such as heterocycles, including imidazole and 1-hydroxybenzotriazole, an anhydride, or a mixed anhydride form acids such as with formic or acetic acid. For example, the reaction is generally carried out in a solvent such as dichloromethane, chloroform, carbon tetrachloride, diethyl ether, THF, and the like. The reaction is typically carried out at temperatures of from 0° C. to reflux temperature of the selected solvent and typically require 1 to 15 hours.

Scheme A, step c, depicts coupling 4-(9-cyclopentyl-7,7-difluoro-5-methyl-6-oxo-6,7,8,9-tetrahydro-5H-pyrimido[5,4-b][1,4]diazepin-2-ylamino)-3-methoxybenzoic acid or a compound of formula (2) with 1-methylpiperidin-4-amine to give 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide. Such coupling reaction to form an amide are well known in the art. Standard amide forming conditions include the use of peptide coupling agents such as, such as 2-(1H-7-azabenzotriazol-1-yl)-1,1,3,3-tetramethyl uronium hexafluorophosphate methanaminium (HATU), dicyclohexylcarbodiimide (DCC), and 1-(3-dimethylaminopropyl)-3-ethylcarbodiimide hydrochloride EDCI). If necessary or desired, an additive such as 4-(dimethylamino)pyridine, 1-hydroxybenzotriazole, and the like may be used to facilitate the reaction. Alternatively, other acylating conditions can be employed, including the use of an acid halide, anhydride, mixed anhydride, or other activating group. Such reactions are generally carried out using a base, such as N-methylmorpholine or triethylamine, in a suitable solvent such as dichloromethane, dimethylformamide (DMF), THF, and the like and are typically carried out at temperatures of from −20° C. to 80° C., and typically require 2 to 48 hours.

The present invention also provides a process for making Form A polymorph of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide, comprising crystallizing 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide from a solvent.

The formation of Form A is largely insensitive to solvent. Suitable solvents include $C_{2-4}$ alkylnitrile, $C_{1-2}$ halocarbons, $C_{3-7}$ alkylacetate, $C_{1-6}$ alcohol, $C_{2-8}$ ether, $C_{3-7}$ alkanone, $C_{6-9}$ aromatic hydrocarbons, and $C_{3-5}$ N,N-dimethylcarboxamide. The selected solvent can contain anti-solvents, that is, a solvent or solvents in which the compound is less soluble than in the crystallization solvent. As used herein the term "$C_{2-4}$ alkylnitrile" refers to a straight or branched alkyl chain having a nitrile, and having a total of from two to four carbon atoms, for example acetonitrile and propionitrile; the term "$C_{1-2}$ halocarbons" refers to halogenated alkanes of from 1 to 2 carbons, such as dichloromethane; the term "$C_{3-7}$ alkylacetate" refers to straight or branched alkly esters of acetic acid having a total of three to seven carbons; the term "$C_{1-6}$ alcohol" a straight or branched alcohols having from one to six carbon atoms, for example methanol, ethanol, n-propanol, iso-propanol, 1,3-propanediol, and the like; the term "$C_{2-8}$ ether" refers to a straight, branched, or cyclic alkyl ethers having a total of from two to eight carbon atoms, for example diethyl ether, methyl-t-butyl ether, THF, dioxane, and the like; the term "$C_{6-9}$ aromatic hydrocarbons" refers to benzene and alkyl substituted benzene, such a toluene, xylene, and the like; the term "$C_{3-5}$ N,N-dimethylcarboxamides" refers to N,N-dimethylamides of a $C_{1-3}$ carboxylic acid, for example N,N-dimethylformamide; the term "$C_{3-7}$ alkanones" refers to a straight or branched alkyl chain having an oxo group and having a total of from three to seven carbon atoms, for example acetone and methyl ethyl ketone.

It is understood that the terms "crystallize," "crystallizing,' and "crystallization" to complete dissolution followed by precipitation and slurry processes that do not involve complete dissolution.

For example, 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A is crystallized form a solvent. The temperature can range form about 40° C. to up to the reflux temperature of the selected solvent and is usually less than 115° C. Where the crystallization involves complete dissolution the rate of cooling is not critical, however, slow cooling is preferred. Slurry processing can be used. The solvent should be one in which 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A is somewhat soluble. The volume of solvent is not critical but should be kept to a minimal amount as a matter of convenience. Optionally, the crystallization may be seeded with Form A. According to the present process Form A 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A may be prepared in substantially pure form. The term "substantially pure" refers to greater than 90%, preferably greater than 97%, and more preferably greater than 99% polymorphic purity.

Form A can be characterized by X-ray diffraction. The peaks were measured using a powder diffractometer equipped with a copper source, primary beam monochromator, and position sensitive detector. The incident beam was collimated using a 1° divergence slit. The source was operated at 40 kV and 30 mA. X-ray powder diffraction data were collected from 3 degrees to 45 degrees a step width of 0.04 degree. The diffractometer was well calibrated with a silicon standard. Form A was found to have the following peaks in degrees 2-theta, rounded to 2 significant figures (relative intensity): 24.89 (65%), 21.78 (100%), 20.87 (39%), 20.35 (41%), 18.70 (50%), 16.40 (31%), 15.75 (29%), and 9.14 (48%). 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A is characterized by peaks at 24.89, 21.78, 20.87, 20.35, 18.70, 16.40, 15.75, or 9.14 degrees 2-theta. Alternately, 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A is characterized by peaks at 24.89 and 21.78; 21.78 and 20.87; 21.78 and 20.35; 21.78 and 18.70; 21.78 and16.40; 21.78 and 15.75; and 21.78 and 9.14 degrees 2-theta. In another embodiments, 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A is characterized by peaks at 24.89, 21.78, and 20.35; 24.89, 21.78, and 18.70; 24.89, 21.78, and 16.40; 24.89, 21.78, and 15.75; and 24.89, 21.78, and 9.14 degrees 2-theta. In still other embodiments, 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A is characterized by peaks at 24.89, 21.78, 20.35, and 9.14; 24.89, 21.78, 18.70, and 9.14; 24.89, 21.78, 16.40, and 9.14; 24.89, 21.78, 15.75, and 9.14; degrees 2-theta.

It is recognized that the relative intensity of X-ray diffraction peaks can be dependent on preferred orientation and other factors. Therefore, a sample of Form A may require processing to mitigate such factors, such as grinding the sample in an agate mortar and pestle or other measures.

Form A can also be characterized by differential scanning calorimetry. A thermogram of Form A provides a single endothermic event at about 241.1 to 241.2 ° C. which was consistent with a melt.

In order that the invention be more fully understood the foregoing processes are exemplified below. These examples are understood to be illustrative only and are not intended to limit the scope of the invention in any way:

PREPARATION 1

Ethyl 3-amino-2,2-difluoropropanoate

H-Benzotriazole-l-methanol (51.0 g, 0.342 mol) was weighed into a round bottom flask and solubilized in EtOH (800 mL). Dibenzylamine (67.5 g, 0.342 mol) was added slowly (over 5 min) to the rapidly stirred solution. Formation of a white precipitate was observed shortly after starting addition. The solution was abandoned to stir for 24 h. At this time the reaction is judged complete by NMR (product fragments on LCMS to show only benzotriazole). The majority of the solvent was removed by rotovap and diethyl ether (1 L) was added to the residue with vigorous stirring. This mixture was filtered, the filtrand washed with ether and dried under vacuum to yield N-(dibenzylaminomethyl)benzotriazole as a fluffy white solid (112 g, quat. yield). $^1$H NMR (400 MHz, chloroform-d) δ ppm 3.80 (s, 4 H) 5.48 (s, 2 H) 7.21 (d, J=8.34 Hz, 1 H) 7.34-7.43 (m, 11 H) 7.49 (d, 1 H) 8.09 (d, J=7.83 Hz, 1 H).

To a suspension of zinc dust (2.7 g, 41.6 mmol) in dry THF (75 mL), stirred under argon atmosphere, was added chlorotrimethylsilane (2.63 mL, 20.8 mmol) followed, 10 min later, by ethyl dibromo-fluoroacetate (3.92 g, 20.8 mmol). After 10 min a slight exotherm was detected. The reaction was left to activate for 1 hour, whereupon it was cooled in an ice bath and a solution of N-(dibenzylaminomethyl)benzotriazole (6.83 g, 20.8 mmol) in THF (50 mL) was added dropwise (over 30 minutes) and then the reaction mixture was allowed to warm to room temperature. After 18 h at r.t., NaHCO3 (sat., 50 mL) was added, let stir for 20 minutes, the reaction was filtered on Celite, and the filter pad was washed with EtOAc. The layers were separated and the aqueous phase was extracted with EtOAc (3×50 mL). The organic layers were combined and washed with 1N HCl (70 mL), brine (70 mL), then dried over MgSO$_4$. After evaporation of the solvent, the residue was poured into rapidly stirring ether (100 mL); the solid formed was removed by filtration and discarded. The ether was evaporated from the filtrate to yield a dark yellow syrup. This crude residue was purified on silica gel column chromatographically (0-10% EtOAc:Hexanes) to yield ethyl 3-(dibenzylamino)-2,2-difluoropropanoate as a clear liquid (3.6 g, 50% yield). $^1$H NMR in CDCl$_3$: (400 MHz) δ ppm 1.18 (t, J=7.07 Hz, 3 H) 3.14 (t, J=13.26 Hz, 2 H) 3.69 (s, 4 H) 4.14 (q, J=7.16 Hz, 2 H) 7.14-7.33 (m, 10 H). [M'H] calc'd for $C_{19}H_{21}F_2NO_2$, 334; found 334.

In a round bottom flask, ethyl 3-(dibenzylamino)-2,2-difluoropropanoate (1.72 g, 5.2 mmol) was solubilized in EtOH (25 mL) and TFA added (0.4 mL, 5.5 mmol). Under an atmosphere of nitrogen Pd(OH)$_2$/C (170 mg of 20% Pd by wt. wet) was added. The reaction mixture was repeatedly purged with nitrogen and then left under hydrogen overnight. At this point the reaction was deemed complete by LCMS, filtered through a pad of Celite, the pad washed with EtOH and the filtrate concentrated without heating to yield ethyl 3-amino-2,2-difluoropropanoate, as its TFA salt, as a foggy syrup which starts to crystallize upon standing (1.31 g, 94% yield). $^1$H NMR (400 MHz, DMSO-d$_6$) δ ppm 1.29 (t, J=7.20 Hz, 3 H) 3.72 (t, J=16.17 Hz, 2 H) 4.34 (q, J=7.24 Hz, 2 H). [M+H] calc'd for $C_5H_9F_2NO_2$, 154; found 154.

PREPARATION 2

4-(9-cyclopentyl-7,7-difluoro-5-methyl-6-oxo-6,7,8, 9-tetrahydro-5H-pyrimido[5,4-b][1,4]diazepin-2-ylamino)-3-methoxybenzoic acid In a round bottom flask, 3-amino-2,2-difluoropropanoic acid (500 mg, 4 mmol) was solubilized in MeOH (10 mL). At 0° C., SOCl$_2$ (1 mL) was added dropwise. The reaction mixture was then stirred at room temperature overnight. Evaporation of the reaction mixture gave methyl 3-amino-2,2-difluoropropanoate, as its HCL salt, as a white solid (570 mg, 81%). $^1$H NMR (400 MHz, DMSO-d$_6$) δ ppm 3.63 (t, J=16 Hz, 2 H) 3.87 (s, 3 H) 9.07 (br. s., 2 H).

To a round bottom flask was added methyl 3-amino-2,2-difluoropropanoate (570 mg, 3.24 mmol), THF (20 mL), cyclopentanone (0.433 mL, 4.87 mmol), and HOAc (1 mL). To this mixture was added sodium triacetoxyborohydride (1.06 g, 5 mmol) portionwise. The reaction was left to stir overnight. It was then added slowly to a stirring solution of ice, NaHCO$_3$ (sat.), and EtOAc. The aqueous layer was further extracted with EtOAc, the organic extracts combined, dried over MgSO$_4$, filtered and concentrated to yield methyl 3-(cyclopentylamino)-2,2-difluoropropanoate as clear syrup (400 mg, 60%). $^1$H NMR (400 MHz, DMSO-d$_6$) δ ppm 1.30 (td, J=13, 6 Hz, 2 H) 1.43 (d, J=8 Hz, 1 H) 1.47-1.70 (m, 4 H) 1.77 (dt, J=12, 6 Hz, 2 H) 3.12 (t, J=6 Hz, 1 H) 3.19 (t, J=14 Hz, 2 H) 3.88 (s, 3 H).

Compound methyl 3-(cyclopentylamino)-2,2-difluoropropanoate (400 mg, 2 mmol) was solubilized in acetone (20 mL, dry). The solution was cooled in an ice water bath under a nitrogen atmosphere and K$_2$CO$_3$ (552 mg, 4 mmol) added. To this, a solution of 2,4-dichloro-5-nitropyrimidine (407 mg, 2.1 mmol) in acetone (5 mL, dry) was added dropwise. The reaction mixture was warmed up to room temperature and stirred for 4 hr. After that, it was diluted with EtOAc and washed by brine and water. The organic extracts were dried over MgSO$_4$, filtered and concentrated to yield methyl 3-((2-chloro-5-nitropyrimidin-4-yl)(cyclopentyl)amino)-2,2-difluoropropanoate which was used directly for next step without further purification. [M+H] calc'd for $C_{13}H_{15}ClF_2N_4O_4$, 365; found 365.

Methyl 3-((2-chloro-5-nitropyrimidin-4-yl)(cyclopentyl) amino)-2,2-difluoropropanoate, was dissolved in AcOH (10 mL). Iron powder (224 mg, 4 mmol) was added followed by the slow addition of HCl (1.5 mL, conc.). The reaction mixture was left to stir at 60° C. for 1 hr. The reaction was then cooled, the stir bar and unreacted iron removed by filtration through paper, and the solvent volume reduced by about 75% on a rotovap. The mixture was then diluted with ice water and EtOAc. Aqueous layer basified by careful addition of sat. NaHCO$_3$. The organic extracts combined, dried over MgSO$_4$, filtered and concentrated to yield 2-chloro-9-cyclopentyl-7, 7-difluoro-8,9-dihydro-5H-pyrimido[5,4-b][1,4]diazepin-6 (7H)-one as a brown syrup (550 mg) which was used directly for next step without further purification. [M+H] calc'd for $C_{12}H_{13}ClF_2N_4O$, 303; found 303.

2-Chloro-9-cyclopentyl-7,7-difluoro-8,9-dihydro-5H-pyrimido[5,4-b][1,4]diazepin-6(7H)-one (550 mg, 1.82 mmol) was dissolved in DMA (10 mL) and cooled in an ice bath. Sodium hydride (80 mg of 60% in mineral oil, 2 mmol) was added slowly and left to stir for 10 minutes. Methyl iodide (0.125 mL, 2 mmol) was then added and the reaction mixture was warmed up to room temperature. After 30 minutes the reaction was deemed complete by LCMS, poured into ice water, the solution extracted with EtOAc. The organic layer washed with brine and water, dried over MgSO$_4$, and concentrated to give 2-chloro-9-cyclopentyl-7,7-difluoro-5-methyl-8,9-dihydro-5H-pyrimido[5,4-b][1,4]diazepin-6(7H)-one as a brown residue which was used directly for next step. [M+H] calc'd for $C_{13}H_{15}ClF_2N_4O$, 317; found 317.

2-Chloro-9-cyclopentyl-7,7-difluoro-5-methyl-8,9-dihydro-5H-pyrimido[5,4-b][1,4]diazepin-6(7H)-one (obtained above), 4-amino-3-methoxy benzoic acid (334 mg, 2 mmol), i-PrOH (10 mL) and conc. HCl (10 drops) were heated to 100° C. overnight. The reaction mixture was then cooled to room temperature, concentrated and redissolved in MeOH, treated with NaOH and refluxed for 1 hr. After which, it was concentrated, acidified with HCl and filtered to give the title as a tan solid (300 mg). [M+H] calc'd for $C_{21}H_{23}F_2N_5O_4$, 448; found 448.

EXAMPLE 1

4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A

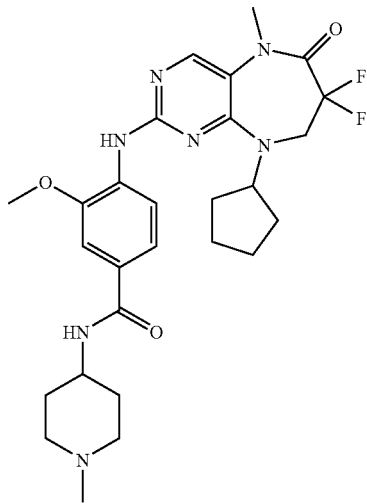

Ethyl 3-(dibenzylamino)-2,2-difluoropropanoate (241 g, 0.72 mol) was dissolved in EtOH (1L) and then 20% Pd(OH)$_2$/C (24 g) and trifluoroacetic acid (60 mL, 0.78 mol) were added. The vessel was repeatedly purged with hydrogen three times and then left under hydrogen (60 psi, 413 kP) and shaken overnight. The mixture was filtered through a pad of Celite®, washed with ethanol and the filtrate was concentrated without heating to give 200 g of compound ethyl 3-amino-2,2-difluoropropanoate which contained a little bit of ethanol.

To a solution of ethyl 3-amino-2,2-difluoropropanoate (401 g, 1.5 mol), cyclopentanone (140 mL, 1.575 mol) and sodium acetate (123 g, 1.5 mol) in THF (6.5 L) was added NaBH(OAc)$_3$ (477 g, 2.25 mol) portionwise over a period of 40 min in ice bath. The resulting mixture was stirred vigorously at room temperature overnight. The mixture was added slowly to a stirring solution of ice (3300 mL), saturated aqueous sodium bicarbonate (3300 mL) and ethyl acetate (3300 mL) cooled in ice-salt bath over a period of 30 min. At this time the layers were separated and the pH of aqueous phase was further adjusted to 11 by addition of 25% aqueous NaOH while cooling in the bath. The aqueous phase was extracted with ethyl acetate (3.5 L×2) and all organic layers were combined, washed with cold saturated NaHCO$_3$ (1.5 L×2), brine (1.5L), dried over MgSO$_4$, filtered and concentrated to give 280 g of ethyl 3-(cyclopentylamino)-2,2-difluoropropanoate.

To a 12 L three-necked flask were charged with ethyl 3-(cyclopentylamino)-2,2-difluoropropanoate (268 g, 1.21 mol) and acetone (2.7 L) and the solution was cooled in ice-salt bath. Then potassium carbonate (337 g, 2.44 mol) was added followed by addition of a solution of 2,4-dichloro-5-nitropyrimidine (260 g, 1.34 mol) in acetone (1.3 L) over a period of 1 h. The resulting mixture was allowed to warm to room temperature slowly and stirred overnight which was monitored by LC-MS. The solvent was removed on rotavapor and the resulting residue was redissloved in water (2 L) and ethyl acetate (2 L). After separation, the aqueous phase was extracted with ethyl acetate (2 L×2) and all organic extracts were combined, washed with water (2 L), brine (2 L), dried over MgSO$_4$ and concentrated. The resulting solid was purified by column chromatography (eluting with hexanes/ethyl acetate=20/1, 15/1 then 10/1) to give 289 g of compound ethyl 3-((2-chloro-5-nitropyrimidin-4-yl)(cyclopentyl)amino)-2,2-difluoropropanoate.

To a solution of ethyl 3-((2-chloro-5-nitropyrimidin-4-yl)(cyclopentyl)amino)-2,2-difluoropropanoate (289 g, 0.763 mol) in acetic acid (1.75 L) in ice bath was added iron powder (86 g, 1.53 mol) followed by addition of conc. HCl (435 mL) over a period of 30 min. The resulting mixture was continued to stir in ice bath for 10 min and then transferred to heating mantle and heated to 60° C. which was monitored by LC-MS. After 5 h, the mixture was concentrated by about 75% and the residue was poured into 3.5 L of ice water and 3.5 L of ethyl acetate. After separation, the aqueous phase was extracted with ethyl acetate (4 L×2) and all organic extracts were combined, washed with saturated sodium bicarbonate (2.5 L), brine (2.5 L), dried over anhydrous sodium sulfate and concentrated. The resulting residue was triturated with ethyl acetate (420 mL) and diethyl ether (3 L) to give 169 g of compound 2-chloro-9-cyclopentyl-7,7-difluoro-8,9-dihydro-5H-pyrimido[4,5-b][1,4]diazepin-6(7H)-one.

2-Chloro-9-cyclopentyl-7,7-difluoro-8,9-dihydro-5H-pyrimido[4,5-b][1,4]diazepin-6(7H)-one (100 g, 0.33 mol) was dissolved in DMA (700 mL) and cooled in ice bath under nitrogen. NaH (14.35 g, 60% in mineral oil, 0.363 mol) was added portionwise over a period of 20 min and the resulting mixture was continued to stir in ice bath for 10 min. Then iodomethane (21 mL, 0.363 mol) was added over a period of 10 min in ice bath and the mixture was stirred in ice bath for 10 min and then allowed to warm to room temperature and stirred for 1 h. The mixture was poured into ice water (2.5 L) and the resulting solid was filtered, washed with water, dried to give 98 g of 2-chloro-9-cyclopentyl-7,7-difluoro-5-methyl-8,9-dihydro-5H-pyrimido[4,5-b][1,4]diazepin-6(7H)-one.

A mixture of 2-chloro-9-cyclopentyl-7,7-difluoro-5-methyl-8,9-dihydro-5H-pyrimido[4,5-b][1,4]diazepin-6(7H)-one (98g, 0.31 mol), 3-methoxy-4-aminobenzoic acid (57 g, 0.341 mol) in i-PrOH (1.05 L) and conc. HCl (30 mL) was heated to reflux for a day. The mixture was cooled to room temperature and the solid was filtered, washed with isopropanol and dried to give 96.5 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid.

A mixture of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (96.5 g, 0.216 mol), N-methyl-4-aminopiperidine (29.3 g, 0.259 mol), HOBt (35 g, 0.259 mol), diisopropylethylamine (45 mL, 0.259 mol)in anhydrous DMF (2.6 L) was cooled in ice bath under nitrogen. EDCI (49.8 g, 0.259 mol) was added and the resulting mixture was allowed to warm to room temperature and stirred overnight. The mixture was poured into ice water (8 L) and ethyl acetate (3 L) and separated. The aqueous phase was extracted with ethyl acetate (4 L×2) and all organic extracts were combined, washed with water, brine, dried over MgSO4 and concentrated. The resulting solid was triturated with diethyl ether to give 47 g of the title compound. DSC peak at 241.42° C.

EXAMPLE 2

4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl) benzamide Form A 2-Chloro-9-cyclopentyl-7,7-difluoro-8,9-dihydro-5H-pyrimido[4,5-b][1,4]diazepin-6(7H)-one (3598 g, 11.89 mol) was dissolved in NMP (11.108 kg) and cooled to about −3° C. A 1 M solution of NaHMDS (11.919 kg, 1.1 eq.) was added over a period of 80 minutes maintaining the temperature below 4° C. Iodomethane (1.858 kg) was added over a period of 10 minutes maintaining the temperature below 35° C. The addition funnel was washed with THF. The temperature was adjusted to 20 to 25° C. and the reaction mixture was stirred for 3 hours. A 1 M solution of NaHMDS (1.2 kg) was added at 23° C. followed by iodomethane (0.188 kg). The addition funnel was washed with THF. The temperature was adjusted to 20 to 25° C. and the reaction mixture was stirred overnight. The temperature was adjusted to 10° C., concentrated aqueous hydrochloric acid (6.42 L), the THF was removed by distillation at reduced pressure, the temperature was adjusted to 20° C., and water (53.3 kg) was slowly added over about 60 minutes maintaining the temperature at about 23 to 25° C. The temperature was adjusted to about 10° followed by stirring overnight. The reaction mixture was filtered, the filter cake was washed with isopropyl alcohol/water (1:1, 2×2 L), and dried in by a stream of nitrogen. The filter cake was dissolved in isopropyl alcohol (4.17 kg) at 76° C., water (20.70 kg) was slowly added over about 85 minutes maintaining the temperature at about 73 to 76° C., after 20 minutes cooled to about 11° over about 3 hours and stir overnight. Collect the solid by filtration, rinse with isopropyl alcohol/water (1:1, 2×1.7 L), and dry under a stream of nitrogen, followed by drying in an oven for 4 days to give 2-chloro-9-cyclopentyl-7,7-difluoro-5-methyl-8,9-dihydro-5H-pyrimido[4,5-b][1,4]diazepin-6(7H)-one.

A mixture of 2-chloro-9-cyclopentyl-7,7-difluoro-5-methyl-8,9-dihydro-5H-pyrimido[4,5-b][1,4]diazepin-6(7H)-one (2.542 kg, 8.05 mol), 3-methoxy-4-aminobenzoic acid (1.50 kg) in t-butyl alcohol (23 L) and heat to about 53° C. Add conc. HCl (951 g) over about 10 minutes, heat to 80° C. and stir for 60 hours. The temperature was adjusted to 15° C. and stirred for 40 hours to give a solid which was collected by filtration, rinsed with isopropyl alcohol/water (1:1, 2×2.5 L) and dried under a stream of nitrogen for about 1.5 hours, then in a vacuum oven at 40° C. for 4 days to give 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid.

A mixture of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (5.125 kg, 6.51 mol), dichloromethane (12 kg), and NMP (0.058 L, 0.09 eq.) was adjusted to 18° C. Thionyl chloride (1.868 kg, 2.4 eq.) was added over about 10 minutes, and eh reaction was stirred at about 18 to 19° C. for 17.5 hours. The temperature was adjusted to 25° C. and the reaction was stirred for 7 hours, adjusted to 18 to 20° C. and stirred for overnight, then 2 days. The dichloromethane was removed by distillation at reduced pressure, toluene (6.2 kg) was added and the distillation continued. About 6 L of dichloromethane were removed. Toluene (6.18 L) was added, the temperature was adjusted to about 20 to 25° C., and a suspension was stirred overnight. The solid was collected by filtration, rinsed with toluene(2×2.12 kg), dried for 3.5 hours in a stream of nitrogen, and then in a vacuum oven at 40° C. for 2 days to give 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid.

Combine 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (3.108 kg, 6.17 mol) and acetonitrile (14.56 kg) and adjust the temperature to about 0° C. Add N-methyl-4-aminopiperidine (0.775 k, 1.1 eq.). Diisopropylethylamine (1.595 kg) was added aver about 29 minutes at temperature of about 6 to 12° C., the temperature was adjusted to about 20 to 25° C. and the reaction mixture was stirred overnight. The solid was collected by filtration, rinsed with acetonitrile (4.47 kg) and dried under at stream of nitrogen for 1 hour, then in a vacuum oven at 40° C. for 2 days to give the title compound.

The title compound (3.35 kg), ethyl alcohol (10.65 kg), and aqueous 2N hydrochloric acid solution were combined at about 20° C. and filtered. Aqueous 2N sodium hydroxide was added and the reaction mixture was stirred at about 20 to 25° C. overnight. Crystals (0.5 g) similar to the ones obtained in Example 1 were added and the stirring continued for 24 hours. Water (5.39 kg) was added and the suspension stirred for 4 hours, filtered, rinsed with water (1.7 kg) and ethyl alcohol (1.7 kg), dried with a stream of nitrogen, and then in a vacuum oven at 40° C. for 3.8 days to give the title compound. DSC peak at 242.12° C.

EXAMPLE 3

4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl) benzamide Form A 4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide (25.6 mg) in dichloromethane (0.5 mL) were combined at 55° C., filtered, and then cooled at 20° C. per hour to ambient temperature and allowed to stand for 16 hours at room temperature, and then cooled to 5° C. overnight to give a solid. The solid was collected by centrifugation, dried in vacuo at ambient temperature to give the title compound.

Form A was also obtained using the procedure of Example 3 and 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide (27.0 mg) in isopropanol (2.5 mL) at an initial temperature of 75° C.

EXAMPLE 4

4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl) benzamide Form A 4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide (29.8 mg) in acetone (6.5 mL) were combined at 55° C., filtered, and then cooled at 20° C. per hour to ambient temperature and allowed to stand for 16 hours at room temperature, and then cooled to 5° C. overnight. The solvent was evaporated under a gentle stream of nitrogen to give a solid, which was dried in vacuo at ambient temperature to give the title compound.

Form A was also obtained using the procedure of Example 4 with 4-(9-cyclopentyl-7,7-difluoro-5-methyl-6-oxo-6,7,8, 9-tetrahydro-5H-pyrimido[4,5-b][1,4]diazepin-2-ylamino)-3-methoxy-N-(1-methylpiperidin-4-yl)benzamide (27.7 mg) in dimethylformamide (0.5 mL) at an initial temperature of 75° C.; 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide (25.4 mg) in dioxane (1.5 mL) at an initial temperature of 75° C.; 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide (23.4 mg) in ethanol (2.7 mL) at an initial temperature of 75° C.; 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide (23.9 mg) in ethyl acetate (10 mL) at an initial temperature of 75° C.; 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide (23.5 mg) in tetrahydrofuran (2.0 mL) at an initial temperature of 55° C.; 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide (24.1 mg) in toluene (15.0 mL) at an initial temperature of 75° C.

EXAMPLE 5

4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A 4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide (27.7 mg) in acetone (6.0 mL) were combined at 55° C., filtered, and then placed in a refrigerator at 5° C. overnight. The solvent was then evaporated under a gentle stream of nitrogen to give a solid, which was dried in vacuo at ambient temperature to give the title compound.

EXAMPLE 6

4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A 4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide (23.6 mg) in dichloromethane (0.5 mL) were combined at 55° C. and filtered. After five minutes heptane (about 0.4 mL) was added dropwise until precipitation was observed, the mixture was slowly cooled at a rate of 20° C. per hour to room temperature and allowed to stand for 16 hours at room temperature, and then placed in a refrigerator at 5° C. overnight give a solid. The solid was collected by centrifugation, dried in vacuo at ambient temperature to give the title compound.

EXAMPLE 7

4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A Combine 4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide (about 33 g) and methanol, add activated charcoal, stir, filter through Celite® and evaporate in vacuo. Then the 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide (32.6 g) is heated in acetone, adding a small amount of methanol to solublize. Add diethyl ether about 10 volumes and cool. Collect the solid by filtration and dry. Melting point: 241-243° C.

Form A can be administered alone or in the form of a pharmaceutical composition. In practice, 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A is usually administered in the form of pharmaceutical compositions, that is, in admixture with pharmaceutically acceptable excipients the proportion and nature of which are determined by the properties of the selected compound of the invention, the chosen route of administration, and standard pharmaceutical practice.

In another embodiment, the present invention provides pharmaceutical compositions comprising: a compound of invention and a pharmaceutically acceptable excipient.

In effecting treatment of a patient in need of such treatment, a compound of the invention can be administered in any form and route which makes the compound bioavailable. 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A can be administered by a variety of routes, including oral and parenteral routes, more particularly by inhalation, subcutaneously, intramuscularly, intravenously, transdermally, intranasally, rectally, vaginally, occularly, topically, sublingually, and buccally, intraperitoneally, intravenously, intraarterially, transdermally, sublingually, intramuscularly, rectally, transbuccally, intranasally, intraadiposally, intrathecally and via local delivery for example by catheter or stent.

One skilled in the art can readily select the proper form and route of administration depending upon the particular characteristics of the compound selected, the disorder or condition to be treated, the stage of the disorder or condition, and other relevant circumstances. The pharmaceutical compositions of the invention may be administered to the patient, for example, in the form of tablets, capsules, cachets, papers, lozenges, wafers, elixirs, ointments, transdermal patches, aerosols, inhalants, suppositories, solutions, and suspensions.

The pharmaceutical compositions of the present invention are prepared in a manner well known in the pharmaceutical art and includes 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A as the active ingredient. The amount of a compound of the present invention may be varied depending upon its particular form and may conveniently be between 1% to about 70% of the weight of the unit dosage form. The term "pharmaceutically acceptable excipient" refers to those typically used in preparing pharmaceutical compositions and should be pharmaceutically pure and non-toxic in the amounts used. They generally are a solid, semi-solid, or liquid material which can serve as a vehicle or medium for the active ingredient. Some examples of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

The present pharmaceutical compositions are preferably formulated in a unit dosage form, each dosage typically containing from about 0.5 mg to about 200 mg of the compounds of the invention. The term "unit dosage form" refers to a physically discrete unit suitable as single dosages, each unit containing a predetermined quantity of active ingredient, in association with a suitable pharmaceutical excipient, by which one or more is used throughout the dosing regime to produce the desired therapeutic effect.

In one particular variation, the composition is a pharmaceutical composition adapted for oral administration, such as a liquid formulation, for example, a solution or suspension, adapted for oral administration or a tablet or a capsule. In still another particular variation, the pharmaceutical composition is a liquid formulation adapted for parenteral administration.

In another embodiment, the invention provides a method of inhibiting a PLK: comprising, contacting the kinase with a compound of the invention. In another embodiment, the invention provides a method of inhibiting a PLK: comprising, administering a compound of the invention to a patient in order to inhibit the kinase in vivo. In a further embodiment, the invention provides a method of inhibiting a PLK: comprising, administering a first compound to a subject that is converted in vivo to a compound of the invention.

In another embodiment, compounds of the invention, including 4-(9-cyclopentyl-7,7-difluoro-5-methyl-6-oxo-6,7,8,9-tetrahydro-5H-pyrimido[4,5-b][1,4] diazepin-2-ylamino)-3-methoxy-N-(1-methylpiperidin-4-yl)benzamide Form A, are provided for use as a medicament. The invention also provides the use of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl) benzamide Form A for the manufacture of a medicament to treat the conditions associated with PLK described herein. The present invention also provides methods of treating conditions associated with PLK, comprising: administering to a patient in need thereof an effective amount of a compound of the invention.

As used herein terms "condition," "disorder," and "disease" relate to any unhealthy or abnormal state. The term "conditions associated with PLK" includes disorders and diseases such as cancer; inflammatory conditions; autoimmune diseases; cardiovascular diseases; infectious diseases; nephrological diseases; neurodegenerative diseases; skin diseases; bone diseases; the protection of proliferating cells; and other conditions. More specifically, a condition associated with PLK is selected from the group consisting of cancer of the breast, ovary, cervix, prostate, testis, esophagus, larynx, stomach, lung, including non-small cell lung cancers, bone, colon, rectum, small intestine, pancreas, thyroid, bladder, liver, kidney, pharynx, tongue, lip, mouth, brain, blood, including leukemias, and skin, including melanomas; psoriasis, alopecia, including chemotherapy agent-induced alopecia and mucositis, multiple sclerosis, colitis, and arthritis; wound healing; cardiovascular diseases, including arterioscleroses, stenoses, restenoses, and hypertrophy; viral, bacterial, fungal and/or parasitic infectious diseases, for example, cytomegalic infections, herpes, hepatitis B and C, Karposi's sarcoma, HIV diseases; nephrological diseases, for example, glomerulonephritis; chronic and acute neurodegenerative diseases, for example, Huntington's disease, amyotrophic lateral sclerosis, Parkinson's disease, AIDS dementia, Alzheimer's disease, ischemias of the brain and neurotraumas; psoriasis ; bone diseases; the protection of proliferating cells, for example, hair, intestinal, blood and progenitor cells from DNA damage caused by radiation, UV treatment and/or cytostatic treatment. Where general terms are used herein to describe conditions associated with PLK it is understood that the more specifically described conditions mentioned in the various diagnostic manuals and other materials are included within the scope of this invention. For example, it is understood that the treatment of inflammatory conditions includes the treatment of arthritis and that arthritis is presently categorized into several more specific disorders, all of which are contemplated by the invention.

The terms "treat," "treatment," and "treating" include improvement of the conditions described herein. Also, it is also recognized that one skilled in the art may affect the conditions by treating a patient presently afflicted with the disorders or by prophylactically treating a patient believed to be susceptible to such conditions with an effective amount of a compound of invention. Thus, the terms "treat," "treatment," and "treating" include all processes providing slowing, interrupting, arresting, controlling, or stopping of the progression of the conditions described herein, but does not necessarily indicate a total elimination of all symptoms or a cure of the condition, and is intended to include prophylactic and therapeutic treatment of such disorders.

As used herein the term "patient" includes humans and non-human animals, for example, mammals, such as mice, rats, guinea pigs, dogs, cats, rabbits, cows, horses, sheep, goats, and pigs. The term also includes birds, fish, reptiles, amphibians, and the like. It is understood that a more particular patient is a human. Also, more particular patients are non-human mammals, such as mice, rats, and dogs.

As used herein, the term "effective amount" refers to the amount of compound of the invention which treats, upon single or multiple dose administration, a patient suffering from the mentioned condition. An effective amount can be readily determined by the attending diagnostician, as one skilled in the art, by the use of known techniques and by observing results obtained under analogous circumstances. In determining the effective amount, the dose, a number of factors are considered by the attending diagnostician, including, but not limited to: the species of patient; its size, age, and general health; the specific condition, disorder, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances. An effective amount of the present use invention, including a compound of the invention, is expected to vary from about 0.1 milligram per kilogram of body weight per day (mg/kg/day) to about 20 mg/kg/day. Specific amounts can be determined by the skilled person.

In a particular embodiment the present invention provides a method for treating cancer, comprising: administering to a patient in need thereof an effective amount of a compound of invention. In a more particular embodiment the present invention provides a method for treating therapy-resistant cancers comprising: administering to a patient in need thereof an effective amount of a compound of the invention.

The invention also provides an article of manufacture: comprising at least one compound of the invention and a label. The label may include information about the manufacturer, doses, conditions to be treated, and the use of the compound or pharmaceutical composition.

In another embodiment the invention provides a kit: comprising, at least one compound of the invention, a label, and apparatus for administration. The apparatus may include mixing vials, liquids for forming solutions or suspensions, tubing, syringes, and the like.

What is claimed is:

1. A process form making 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide Form A characterized by peaks at 24.89, 21.78, 20.87, 20.35, 18.70, 16.40, 15.75, or 9.14 degrees 2-theta: comprising crystallization of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide from a solvent selected from the group consisting of $C_{2-4}$ alkylnitrile, $C_{3-7}$ alkylacetate, $C_{1-6}$ alcohol, $C_{2-8}$ ether, $C_{3-7}$ alkanone, $C_{6-9}$ aromatic hydrocarbons, and $C_{3-5}$ N,N-dimethylcarboxamide.

* * * * *